(12) United States Patent
Wang

(10) Patent No.: US 11,491,300 B2
(45) Date of Patent: Nov. 8, 2022

(54) ROBOT-CONNECTED IOT-BASED SLEEP-CARING SYSTEM

(71) Applicant: Xiamen Brana Design Co., Ltd., Fujian (CN)

(72) Inventor: Zhongtang Wang, Xiamen (CN)

(*) Notice: Subject to any disclaimer, the term of this patent is extended or adjusted under 35 U.S.C. 154(b) by 795 days.

(21) Appl. No.: 16/406,025

(22) Filed: May 8, 2019

(65) Prior Publication Data

US 2019/0358428 A1 Nov. 28, 2019

(30) Foreign Application Priority Data

May 23, 2018 (CN) .......................... 201810568725.9

(51) Int. Cl.
*G06F 17/00* (2019.01)
*A61M 21/02* (2006.01)
*B25J 9/16* (2006.01)
*B25J 11/00* (2006.01)
*B25J 13/00* (2006.01)
*B25J 13/06* (2006.01)
*G06F 21/60* (2013.01)
*H04L 9/32* (2006.01)
*H04L 12/28* (2006.01)
*H04L 67/125* (2022.01)
*A61M 21/00* (2006.01)
*H02J 7/00* (2006.01)
*H02J 7/02* (2016.01)
*H04L 9/00* (2022.01)

(52) U.S. Cl.
CPC .............. *A61M 21/02* (2013.01); *B25J 9/163* (2013.01); *B25J 9/1676* (2013.01); *B25J 9/1694* (2013.01); *B25J 11/008* (2013.01); *B25J 11/009* (2013.01); *B25J 13/003* (2013.01); *B25J 13/006* (2013.01); *B25J 13/06* (2013.01); *G06F 21/602* (2013.01); *H04L 9/3263* (2013.01); *H04L 12/282* (2013.01); *H04L 12/2825* (2013.01); *H04L 12/2827* (2013.01); *H04L 67/125* (2013.01); *A61M 2021/0027* (2013.01); *A61M 2021/0044* (2013.01); *A61M 2205/3584* (2013.01); *A61M 2205/3592* (2013.01); *A61M 2205/505* (2013.01); *A61M 2230/04* (2013.01); *A61M 2230/205* (2013.01); *A61M 2230/43* (2013.01); *A61M 2230/63* (2013.01); *H02J 7/0042* (2013.01); *H02J 7/025* (2013.01); *H04L 9/50* (2022.05); *H04L 2012/2841* (2013.01)

(58) Field of Classification Search
IPC ...................................................... A61M 21/02
See application file for complete search history.

(56) References Cited

U.S. PATENT DOCUMENTS 8,449,471 B2 * 5/2013 Tran .................... A61B 5/14532
600/485
9,775,520 B2 * 10/2017 Tran ........................ G16H 50/20
(Continued)

*Primary Examiner* — Evral E Bodden
(74) *Attorney, Agent, or Firm* — Raymond Y. Chan; David and Raymond Patent Firm

(57) ABSTRACT

A robot-connected IoT-based sleep-caring system includes a sleep-caring robot and an IoT system. The sleep-caring robot includes environment monitoring, physiology monitoring, sleep monitoring, sound, lighting and electricity control, a smart storage compartment, central data processing, and machine arms. The IoT system senses and executes instructions from the sleep-caring robot, thereby catering to bedroom activities of the user.

26 Claims, 7 Drawing Sheets

(56) References Cited

U.S. PATENT DOCUMENTS

| | | | |
|---|---|---|---|
| 10,357,881 B2* | 7/2019 | Faridi | H04N 5/23219 |
| 10,492,721 B2* | 12/2019 | Yoon | A61B 5/0816 |
| 2017/0206064 A1* | 7/2017 | Breazeal | G06F 8/34 |

* cited by examiner

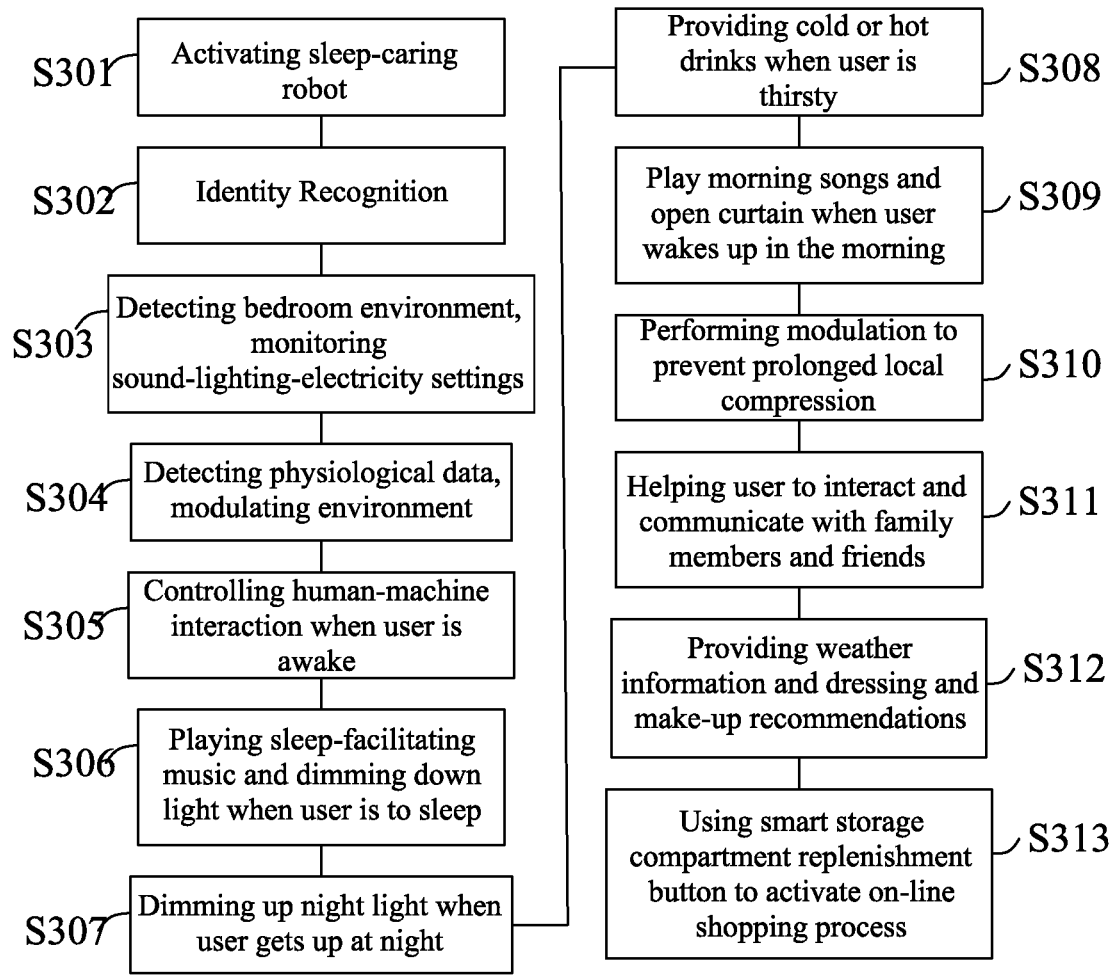
F I G. 10

ROBOT-CONNECTED IOT-BASED SLEEP-CARING SYSTEM

BACKGROUND OF THE INVENTION

1. Technical Field

The present invention relates to robots, and more particularly to a sleep-caring robot working in an IoT (Internet of Things) system.

2. Description of Related Art

One third of a person's life spends on sleep, and therefore sleep quality is significant to human well-being.

According to survey conducted by the China Sleep Research Society, among all the adults in China, 50.3% suffer from sleep problems, and 38.2% are troubled by sleeplessness, with symptoms such as dreamful sleep, difficult falling asleep, and waking up tired. Globally, about one third of people are not sleeping well.

A bedroom is the primary domain where sleep is performed. Thus, the temperature, humidity, air, smell, voice, lighting, bedding, safety and other environmental factors in the bedroom indeed matter to sleep quality. The awake stage, the sleep stage, and the waking stage each have different requirements in terms of bedroom environment. Adjustment depending on manual operation is hard to be accurate and is necessarily an interference with sleep.

In particular, young children and bedridden patients who lack for self-care ability have even demanding requirements for bedroom and supply environment, and they conventionally need special care from dedicated guardians. Such a practice causes a heavy burden to both the healthy adult guardians, depriving them of proper rest, good sleep, and normal daily work and life.

In view of this, there is a need for a smart sleep-caring robot designed with advanced technology so that it can monitor bedroom environment, users' physiological features and sleep stage according to users' habits and perform autonomous decision-making to adjust sound, lighting, electricity, and air environment dynamically in a bedroom a real time manner and to configure a smart storage compartment, thereby catering for users' basic material demands for their sleep-caring and living activities. In addition, the system may have smart appliances, smart furniture, smart wearable devices, a smart security system, a family healthcare robot, and an emotional accompanying robot interconnected through a wireless network, for sensing and executing instructions from the sleep-caring robot, so as to satisfy users' daily life needs in a personalized manner, thereby facilitating high quality sleep and good rest, and in turn improving bedroom life experience and comfort.

SUMMARY OF THE INVENTION

The objective of the present invention is to provide a robot-connected IoT-based sleep-caring system, which caters for users' bedroom living activities, so as to provide high quality sleep and good rest, thereby improving bedroom life experience and comfort.

To achieve the foregoing objective, the present invention adopts the following technical schemes:

A robot-connected IoT-based sleep-caring system comprises a sleep-caring robot and an IoT system;

the sleep-caring robot including a power supply driving module, an obstacle avoiding module, an identity recognition module, a personal data encryption module, built-in sensors, machine arms, an environment monitoring module, a physiology monitoring module, a sleep monitoring module, a voice control module, a light control module, an appliance control module, a central touch screen display, a mobile smart control terminal, a smart storage compartment, a wireless communication module, a central data processing module, a human-machine interface module, a remote monitoring/interacting module, through monitoring bedroom environment of a user and physiological data of the user, learning bedroom living habits of the user, adjusting sound, lighting, electricity and air in a bedroom to desirable working conditions, and providing bedroom supplies, thereby catering to bedroom activities of the user; and the IoT system including smart appliances, smart furniture, smart wearable devices, a mobile smart terminal, a smart security system, a housekeeping robot, and an emotional accompanying robot that are all interconnected through a wireless network, having its working condition data sent to the central data processing module of the sleep-caring robot through the wireless communication module, and receiving and responding to instructions from the sleep-caring robot.

The power supply driving module includes a power supply and a servomotor driving system, serving to supply electricity so as to drive the sleep-caring robot to perform various acts accurately; the power supply including a charging device and a power-storing device, both located in a lower part of the sleep-caring robot; the charging device matching a wired charging pile and a wireless charging zone, wherein the wired charging pile and the wireless charging zone are for the sleep-caring robot to go to and get charged automatically when the power-storing device has a power level lower than a predetermined power threshold, and the sleep-caring robot returns to a designated standby area when it is fully charged.

The obstacle avoiding module includes a positioning unit, an electronic fence, and ultrasonic radars, the positioning unit being based on GPS (Global Positioning System) and Beidou Navigation and setting the electronic fence to define an area for the sleep-caring robot to work, and providing information of static obstacles in the area defined by the electronic fence, the ultrasonic radars being installed peripherally on the sleep-caring robot, for detecting distances to surrounding obstacle, so that the obstacle avoiding module according to data from the positioning unit and the ultrasonic radar guides the sleep-caring robot away from surrounding dynamic and static obstacles, thereby helping the sleep-caring robot to arrive at a predetermined location.

The identity recognition module performs real-name authentication using blockchain technology, the user entering a smart contract, creating a personal private key and a personal public key, sending the personal public key, biometric information, and ID (Identity) card information to a blockchain network, so as to generate blocks and acquire a link to the public key certificate, the user inputting the biometric information, and the blockchain network identifying the user by verifying the link to the public key certificate; the biometric information including but not limited to a fingerprint, a voice print, a peripheral venous network and a human face.

The personal data encryption module creates a user personal data center using blockchain technology, the user personal data center storing and running personal and family data of the user in a distributed manner; the personal data center, the sleep-caring robot, the Internet, the IoT system, and a public cloud being all connected based on the smart contract for the blockchain authorized by the user, the personal and family data being written into the blocks in a real time manner, and being published to the blockchain in the public cloud with authorization from the user, so as to achieve security isolation of the personal and family data; and a third party having authorization being allowed to access the data.

The machine arms are each structurally similar to a human upper limb, and are attached to an upper end of the sleep-caring robot, one at each side, each said machine arm having one end connected to the sleep-caring robot, and an opposite end formed as a machine hand, the machine hand including 5 fingers, the machine arms receiving instructions from the central data processing module, and being driven by the servomotor to perform acts.

The environment monitoring module includes environment monitoring sensors, A/D (Analog-to-Digital) conversion circuit, and is installed in a head of the sleep-caring robot, environment data detected by the environment monitoring sensors being sent to the central data processing module; the environment monitoring sensors including but not limited to a temperature sensor, a humidity sensor, a noise sensor, a smoke sensor, a PM (Particulate Matter) 10 sensor, a PM2.5 sensor, a carbon dioxide sensor, a carbon monoxide sensor, and a smell sensor.

The physiology monitoring module integrates a plurality of monitoring sensors for collecting physiological data of the user in a non-contact manner, the monitoring sensors including but not limited to a body temperature sensor, a pulse sensor, a breath sensor, a blood pressure sensor, an oxygen saturation sensor, an electrocardiogram sensor, and a limb motion sensor, the monitoring sensors sending the detected physiological data to the central data processing module through the A/D conversion circuit;

the breath sensor collecting infrared-detected data about heave of the user's chest and abdomen during inhalation and exhalation, so that breath frequency and breath depth of the user can be calculated; and the monitoring sensors being installed on finger backs of the machine hand, determining the user's state, and turning the monitoring sensors to face the user's neck and hands when conducting detection.

The sleep monitoring module includes an image sensor installed in a head of the sleep-caring robot, and a brainwave monitoring sensor, a muscle tone monitoring sensor, and a snore monitoring sensor installed on finger backs of the machine hand, all of a non-contact type;

the image sensor having a visible-light image capturing mode and an infrared image capturing mode, and sending image data of the user to the central data processing module, for real-time recognition and determination of body location information of the user;

the brainwave monitoring sensor acquiring electroencephalogram of the user, and sending data to the central data processing module, for determination of whether the user is awake or asleep, and is in which sleep stage;

the muscle tone monitoring sensor acquiring a muscle tone level at the user's neck, and upper and lower limbs, and sending data to the central data processing module, for determination of in which sleep stage the user is; and the snore monitoring sensor acquiring data about the user's snore sound and rhythm, and sending the data to the central data processing module, for determination of in which sleep stage the user is and times of the user's sleep apnoea.

The voice control module includes a voice hearing unit and a smart speaker, and is installed in a head of the sleep-caring robot, the voice hearing unit collecting voice signals from the user so as to obtain voice data, and sending the data to the central data processing module through the wireless communication module, recognizing speaking voice, understanding language, and giving out instructions, the smart speaker receiving the instructions through the wireless communication module, and executing options of content to be played and playing methods, the smart appliances, smart furniture, and family healthcare robot that are connected wirelessly receiving and responding to instructions;

the smart speaker being further connected to the sleep monitoring module through the wireless communication module, so as to adjust the content to be played and volume according to the sleep stage and following a predetermined program; and the predetermined program being set by the user or a guardian.

The light control module is installed in a head of the sleep-caring robot, and includes a smart sensing unit, a control unit and smart lamps; the smart sensing unit including a luminous intensity sensor, a light color sensor, and a color temperature sensor, and transmitting data collected to the central data processing module, so as to control the smart lamps through the control unit according to triggering conditions of scene modes; the control unit allowing the user to name, add or delete each of the smart lamps in the central touch screen display or in the smart control terminal; and the control allowing each said lamp to be turned on, turned off, dimmed and changed in color.

The scene modes include human-machine interaction, clock setting, sleep stage, and third party mobile smart terminal control, wherein human-machine interaction is set as the first priority, and clock setting is set as the second priority, while an authorized third party making control through a mobile smart terminal with a contract is set as the third priority.

The appliance control module is installed in a head of the sleep-caring robot is rotatable up to 180 degrees in both directions, and performs near-field control using Bluetooth and infrared, and performs far-field control using Wi-Fi Wireless Fidelity).

The central touch screen display is installed in an upper front part of a frunk of the sleep-caring robot, for displaying aggregate data, security monitoring signals, TV (Television) signals, video playing, and touch operation.

The smart storage compartment is located in a lower-middle part of a trunk of the sleep-caring robot, and is divided into an upper-left partition, an upper-right partition, a lower-left partition, and a lower-right partition;

the upper-left partition storing non-private articles, with its side walls and top equipped with sensors, which collect information about articles put in or taken out data, the information then being transmitted to the central data processing module, for the central data processing module to retrieve information about types and quantities of the articles stored, and to show the information as a structured data chart displayed in a touch screen located outside a transparent door of the partition;

the lower-right partition storing private articles, with its door equipped with a smart lock, and with its side walls and top equipped with sensors, which collect information about articles put in or taken out data, the information then being transmitted to the central data processing module, for the central data processing module to retrieve information about types and quantities of the articles stored, and to show the information as a structured data chart displayed in a touch screen located inside an opaque door of the partition in a real time manner;

the lower-left partition being configured as a temperature-controllable chill box, the upper-right partition being configured as a temperature-controllable thermotank, the partition containing therein a temperature sensor, a pressure sensor, and an image recognition sensor, and transmitting data collected to the central data processing module, for the central data processing module to retrieve information about types, quantities and weight of the articles stored and internal temperature data, and to show the information in a touch screen outside a door of the partition; and the touch screen further having a replenishment button, and pushing the replenishment button leading to commencement of an on-line shopping process; the touch screen further having a voice button, and pushing the voice button making the smart speaker broadcast information of the structured data chart.

The central data processing module is located in an upper part of a trunk of the sleep-caring robot, for receiving data detected by the built-in sensors of the sleep-caring robot and external sensors, and fuses information from multiple sensors to sense states of the sleep-caring robot, of bedroom environment, of the user, and of security monitoring, through the human-machine interface module, the central data processing module smartly controlling the sleep-caring robot, the smart appliances connected through the wireless network, smart furniture, the housekeeping robot, and the emotion robot; and according to the user's instructions to send raw data as collected and processed data to the blockchain in the public cloud for storage or operation.

The human-machine interaction interface module includes a human-machine interface device, interaction technology, monitoring technology, remote operation technology, communication technology, completing cognitive learning, automatic organization, fuzzy information processing; the interaction technology including recognition of user-initiated requests and recognition of non-user-initiated requests, the user-initiated requests include voice, lip language, gestures, controllers, remote control; the non-user-initiated requests include setting specific triggering conditions, the user instinctively sending physiology feedback signals through the smart wearable connected to the wireless network; and the human-machine interaction interface module further includes brain-computer interface mode, which collects the user's brain bioelectric activity signals through non-invasive sensors, and transmits data to the central data processing module, for control of the sleep-caring robot.

The smart appliances connected through the wireless network include a smart air conditioner, a smart air cleaner, a smart toilet, a smart water heater, a smart TV, a smart refrigerator, a smart washing machine, and a smart mosquito killer, through the appliance control module, the machine arms receiving and responding on instructions from the central data processing module; and the smart furniture connected through the wireless network includes a smart closet, a smart bed, a smart mattress, a smart pillow, a smart curtain, a smart door and a smart window, its smart sensing device, through the wireless communication module, receiving and responding to instructions from the central data processing module; the smart furniture naming, the user adding or deleting the smart furniture in the central touch screen display or the mobile smart control terminal.

The security monitoring system connected to the wireless network includes infrared detectors, smoke detectors, gas detectors, and cameras. They collect data and the data are sent to the central data processing module through the wireless communication module to be displayed in the central touch screen display and the mobile smart control terminal as a structured data chart in a real time manner.

The smart wearable devices include a smart wristband, a smart watch, a smart ankle bracelet, a smart earring, a smart eyeshade, a smart earpiece, smart glasses, smart pajamas, a smart hat, smart socks, and a smart patch, and data they detect are sent to the central data processing module through the wireless communication module. The user can name, add or delete the smart wearable devices in the central touch screen display or the mobile smart control terminal.

The mobile smart control terminal works as the remote control of the sleep-caring robot, and also works as a smartphone, while it can be replaced with a laptop computer, a smartphone, a smart vehicle, smart glasses, or a smart watch.

The wireless communication module uses infrared transmission, RFID (Radio Frequency Identification), Bluetooth for near-field communication, and uses Wi-Fi for remote communication.

The remote monitoring/interacting module allows an authorized third party to acquire data of the sleep-caring robot using the mobile smart terminal for which it enters a contract through the wireless communication module in a real time manner, so as to operate and monitor the sleep-caring robot remotely; the third party include legal guardian, contracted care-giver, contracted emergency medical service provider.

The learning bedroom living habits of the user is achieved by having the sleep-caring robot recognize and analyze the user's bedroom sound, lighting, electricity environment data, physiology monitoring data, sleep behavior data, human-machine interaction data, supply consumption data, and event-specific triggering data stored in the blockchain in the public cloud, sense the user's bedroom living habits, perform self-learning, perform autonomous decision-making, set resulting decision as benchmarks, collect the user's feedback data about the benchmarks set by the sleep-caring robot based on its autonomous decision-making, identify differences, perform self-learning, perform autonomous decision-making, and repeat, so as to achieve harmony between the user and the sleep-caring robot.

The user is a young child, a bedridden patient, or a healthy adult, and includes one or more persons, in which when the user includes plural persons, identity recognition and physiological data monitoring, operating, encrypting and storing, respectively.

A young child sleep-caring service process includes:

a guardian entering a smart contract, activating the sleep-caring robot; performing identity recognition; the sleep-caring robot monitoring bedroom environment, controlling the smart appliances and furniture, adapting sound, lighting, electricity environment to a mode set by the guardian; the sleep-caring robot monitoring user physiological data, determining the user's state, adjusting sleeping environment in a real time manner, the smart speaker playing music until the user falls asleep, stopping music playing and turning off light; when the user cries for hunger, the machine hand taking out milk, helping the user to have milk, taking out a toy for the user to play; a mobile smart terminal of the guardian showing the user's state in a real time manner; a smart patch on a paper diaper showing monitoring data, giving out alarm, warning the guardian to change the user's diaper.

A bedridden patient-specific sleep-caring service process includes:

activating the sleep-caring robot; performing user identity recognition; the sleep-caring robot monitoring bedroom environment, controlling the smart appliances and furniture, adapting sound, lighting, electricity, and air environment to the user's habits or a mode set by the user; the sleep-caring robot monitoring the user's physiological data, determining the user's state, adjusting bedroom environment in a real time manner according to the monitoring data; the smart speaker playing music until the user falls asleep, stopping music playing and turning off light, up loading data to the blockchain in the public cloud; when the user feels hungry, the machine hand taking out food, helping the user to eat and drink; when the user urinates and/or defecates, instructing and helping a family healthcare robot and the smart furniture to clean excrement and clean the user's perineum; according to a set program, taking out medicine and drinking water and prompting and helping the user to take medicine timely; smart pajamas monitoring the user's body position, adjusting the smart mattress, so as to prevent pressure sore caused by prolonged local compression; the user interacting with family members and friends through the smart speaker; a guardian using a mobile smart terminal for which it enters a contract to see the user's state and communicate with the user in a real time manner and performing monitoring and control remotely and when abnormal physiological data are detected, reporting to a competent third party for timely assistance.

A healthy adult sleep-caring service process includes:

a user activating the sleep-caring robot using a near-field or remote manner; the sleep-caring robot adjusting bedroom smart appliances and smart furniture according to the user's habits or human-machine interaction instructions; the user going to bed, determining the user's state, further performing real time adjustment until the user falls asleep, stopping music playing and turning off light; when the user wakes up, activating the sound, lighting and electricity settings for gradually awaking; when the user gets up, providing weather information, and instructing the smart closet to provide dressing and make-up recommendations.

BRIEF DESCRIPTION OF THE DRAWINGS

FIG. 10 shows a healthy adult-specific flow of the present invention.

DETAILED DESCRIPTION OF THE INVENTION

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

Referring to FIG. 1 through FIG. 10, the present invention discloses a robot-connected IoT-based sleep-caring system, which comprises a sleep-caring robot and an IoT system.

Figure 1:
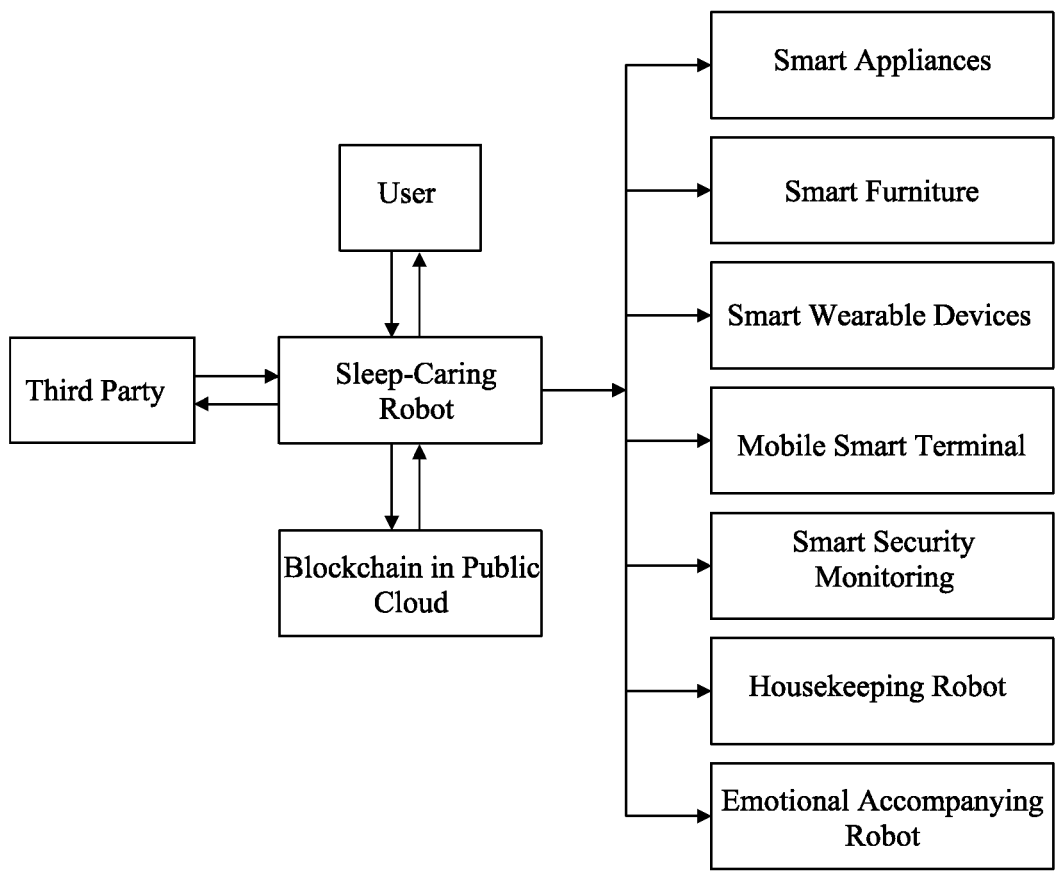
FIG. 1 is a block diagram of a robot-connected IoT-based sleep-caring system according to the present invention.

Referring to FIG. 1, the participating parties of the robot-connected IoT-based sleep-caring system include: a user, a sleep-caring robot, a third party, a blockchain in a public cloud, and web-based smart devices.

The user performs human-machine interaction with the sleep-caring robot by means of identity recognition. The identity recognition uses blockchain technology to perform real-name authentication. The user enters a smart contract to create a personal private key and a personal public key. The personal public key, biometric information and ID card information are sent to a blockchain network, so as to generate blocks and acquire a link to the public key certificate. The user inputs the biometric information, and the blockchain network identifies the user by verifying the link to the public key certificate.

The third party includes a user guardian, a contracted care-giver, or a contracted emergency medical service provider, who controls the sleep-caring robot through a mobile smart terminal for which a contract has been entered.

The web-based smart devices include smart appliances, smart furniture, smart wearable devices, a mobile smart terminal, smart security monitoring, a housekeeping robot, and an emotional accompanying robot, having its working condition data sent to the central data processing module of the sleep-caring robot through the wireless communication module, and receiving and responding to instructions from the sleep-caring robot.

The user's personal data is encrypted, stored, and operated using public-cloud-based blockchain technology. A user personal data center is built for storing and operating the user's personal and family data in a distributed manner. The personal data include monitoring data from the sleep-caring robot, operational data of the web-based smart device, and interaction data between the user/third party and the sleep-caring robot. The personal data center, the sleep-caring robot, the Internet, the IoT system, and a public cloud are all connected based on the smart contract for the blockchain authorized by the user. The personal and family data are written into the blocks in a real time manner, and are published to the blockchain in the public cloud with authorization from the user, so as to achieve security isolation of the personal and family data. The third party is allowed to access the data when it is authorized to do so.

Figure 2:
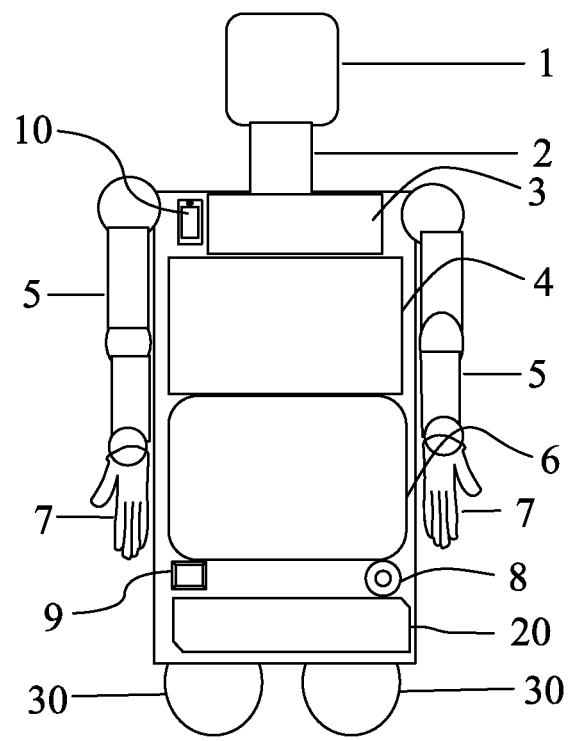
FIG. 2 is a schematic drawing of a sleep-caring robot according to the present invention.

Referring to FIG. 2, the sleep-caring robot has a human-like structure, and includes a head 1, a neck 2, a trunk, two machine arms 5, two machine hands 7, and wheeled legs 30. The head 1 is rotatable up to 180 degree in both directions about the neck 2.

The trunk at its upper part houses a central data processing module 3, which receives data monitored by sensors inside and outside the sleep-caring robot, and fuses information from these sensors to sense states of the sleep-caring robot, of bedroom environment, of the user, and of security monitoring. Through the human-machine interface module, the central data processing module 3 smartly controls the sleep-caring robot, the smart appliances and smart furniture connected through the wireless network, the housekeeping robot, and the emotional accompanying robot. The central data processing module 3 according to the user's instructions sends the collected raw data and processed data to the blockchain in the public cloud for storage and operation.

The central data processing module 3 further performs real-time analysis of the user's bedroom sound, lighting, electricity environment data, physiological feature monitoring data, sleep behavior data, human-machine interaction data, supply consumption data, and event-specific triggering data stored in the blockchain in the public cloud and senses the user's bedroom living habits to perform self-learning and autonomous decision-making. It collects the user's feedback data about the results of the autonomous decision-making performed by the sleep-caring robot, and accordingly performs self-learning and future autonomous decision-making. By repeating this process, harmony between the user and the sleep-caring robot can be achieved.

The trunk at its upper part is installed with a mobile smart control terminal 10, which works as a remote control of the sleep-caring robot, and also works as a smartphone. The user can carry the mobile smart control terminal 10 with him/her, so as to control the sleep-caring robot remotely in any place in the bedroom. Similarly, a third party who has entered a smart contract and thereby obtained authorization can use its contracted mobile smart terminal in lieu of the mobile smart control terminal 10 and acquire data of the sleep-caring robot in a real time manner through the wireless communication module, so as to operate and monitor the sleep-caring robot remotely.

The trunk at its upper-middle front wall is provided with a central touch screen display 4, and at its lower-middle part formed with a smart storage compartment 6.

The trunk at its lower-middle part peripherally is equipped with ultrasonic radars 8 and a positioning unit 9. The ultrasonic radars 8 are distributed around the sleep-caring robot for detecting distances to surrounding obstacle. The positioning unit 9 sets the electronic fence based on GPS and Beidou Navigation, to define an area for the sleep-caring robot to work, and to provide information of static obstacles in the area defined by the electronic fence. According to data from the positioning unit 9 and the ultrasonic radars 8, the sleep-caring robot can be guided away from peripheral obstacles, either dynamic or static, and arrive at a predetermined location.

The trunk at its lower part houses a power supply 20, which powers the sleep-caring robot.

Figure 3:
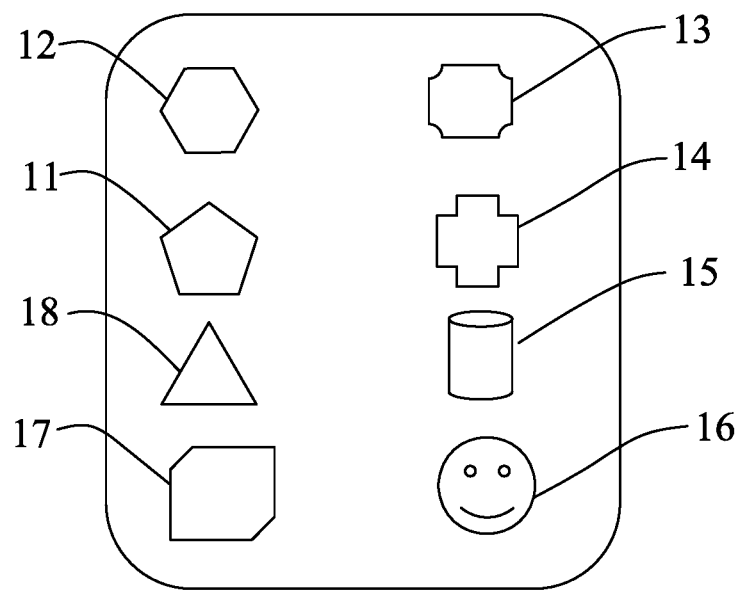
FIG. 3 is a schematic drawing of a head of the sleep-caring robot according to the present invention showing functional modules thereon.

Referring to FIG. 3, the head 1 includes an environment monitoring module 11, a physiological detection module, a voice monitoring module 12, a light control module 13, an appliance control module 14, a smart speaker 15, a human-machine interaction interface module 16, a wireless communication module 17, and a remote monitoring/interacting module 18.

The environment monitoring module 11 uses environment monitoring sensors to collect data about the bedroom environment and sends the data to the central data processing module 3. The environment data monitored by the environment monitoring sensors include the temperature, humidity, noise level, smoke, PM10, PM2.5, carbon dioxide level, carbon monoxide level, and various smells in the bedroom.

The voice monitoring module 12 collects the user's voice signals so as to obtain voice data, and sends the data through the wireless communication module 17 to the central data processing module 3. The central data processing module 3 then recognizes speaking voice, understands language, and gives out instructions. Through the wireless communication module 17, the smart speaker 15 receives these instructions, and executes options of content to be played and playing methods. Similarly, the wirelessly connected smart appliances, smart furniture, smart wearable devices, family healthcare robot, and emotional accompanying robot receive and respond to the instructions.

The light control module 13 includes a smart sensing unit, a control unit and smart lamps. The smart sensing unit uses luminous intensity sensors, light color sensors and color temperature sensors to collect data, and transmits the data to the central data processing module 3. The central data processing module 3 then according to the scene mode triggering conditions, controls turning on, turning off, dimming and color changing of each of the lamps through the control unit. The user can name, add or delete the smart lamps in the central touch screen display 4 or the smart control terminal 10. The scene modes available may include human-machine interaction, clock setting, awake, about to sleep, sleep, waking up and third party mobile smart terminal control. Wherein, human-machine interaction is set as the first priority, and clock setting is set as the second priority, while an authorized third party making control through a mobile smart terminal with a contract is set as the third priority.

The appliance control module 14 uses infrared transmission and Bluetooth to perform near-field communication, and uses Wi-Fi to perform remote communication. Wherein, the infrared transmission is the primary control mode of the bedroom smart appliances. For this purpose, an infrared transmitter is connected to an MCU (Microcontroller Unit) to send remote control signals to appliances. An infrared receiver is also connected to the MCU to learn the infrared remote control encoding rules of the appliances. The wireless communication module 17 is connected to the MCU to receive control instructions from the sleep-caring robot.

The smart speaker 15 is further connected to the sleep monitoring module through the wireless communication module 17. According to whether the user is awake or in which sleep stage the user is in, music is played through the smart speaker 15 with the content and volume conforming to the program set by the user or the guardian through the human-machine interaction module 16.

The human-machine interaction interface module 16 includes a human-machine interface device, interaction technology, monitoring technology, remote operation technology, and communication technology. By means of cognitive learning, automatic organization, and fuzzy information processing, it enables the sleep-caring robot to communicate information with the user, to recognize and understand the user's intention, and to respond thereto. The user may initiate his/her request through voice, lip language, gestures, a controller, or a remote control. Alternatively, the user may cause non-user-initiated requests through setting specific triggering conditions or instinctive physiological feedback signals from smart wearable devices connected to the wireless network.

The human-machine interaction interface module 16 further includes a brain-computer interface mode, which collects the user's brain bioelectric activity signals through non-invasive sensors, and transmits data to the central data processing module 3, for controlling the sleep-caring robot.

The wireless communication module 17 includes means of infrared transmission, RFID, and Bluetooth for near-field communication, and means of Wi-Fi for remote communication.

With the remote monitoring/interacting module 18, a third party who has entered a smart contract and thereby obtained authorization can use a mobile smart terminal for which the contract is entered to acquire data of the sleep-caring robot through the wireless communication module 17 in a real time manner, so as to operate and monitor the sleep-caring robot remotely. The third party includes a guardian, a contracted care-giver, and/or a contracted emergency medical service provider.

Figure 4:
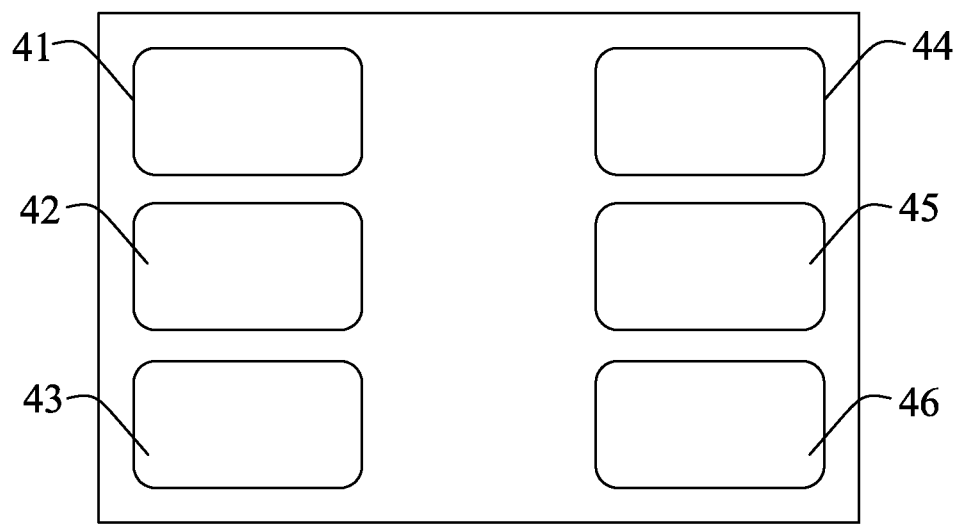
FIG. 4 shows interface displayed in a central touch screen display located in the upper front of the sleep-caring robot of the present invention.

Referring to FIG. 4, the central touch screen display 4 displays aggregate bedroom environment data 41, user physiology monitoring data 42, data 43 about articles in the smart storage compartment 6, security monitoring signals 44, TV program titles 45, and video titles 46 in a real time manner, for the user or a guardian to make selection through touch operation, or to perform remote control through the mobile smart control terminal.

Figure 5:
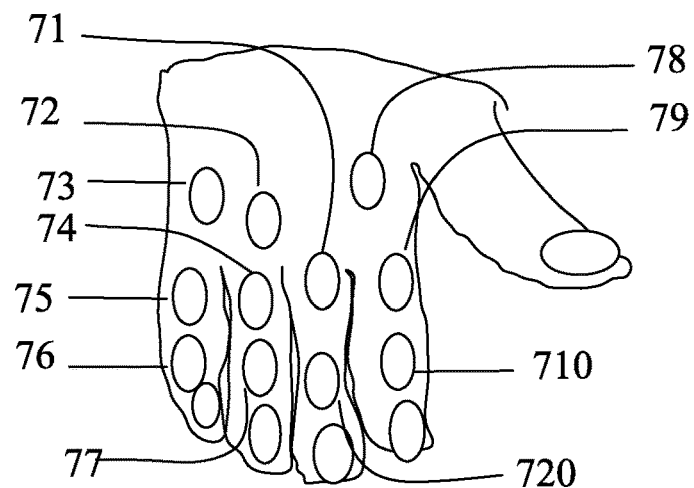
FIG. 5 is a schematic drawing of a machine hand of the sleep-caring robot according to the present invention showing functional modules provided on finger backs.

Referring to FIG. 5, the machine hand 7 is at the free end of the machine arm 5 and has a human-hand-like design. It includes 5 fingers, and receives instructions from the central data processing module 3, and is driven by the servomotor to perform acts; the physiology monitoring module has monitoring sensors, integrated in the machine hand 7 for collecting the user's physiological data in a non-contact manner.

Particularly, an image sensor 71, a brainwave monitoring sensor 72, a muscle tone monitoring sensor 73 and a snore monitoring sensor 74 are respectively installed on the finger backs for collecting the user's data. The data they collect are sent to the central data processing module 3 for determination of the user's sleep state. The image sensor 71 may include a visible light image acquiring mode and an infrared image acquiring mode, for working in lightness and dimness, respectively, to recognize and determine the user's body location in a real time manner. The brainwave monitoring sensor 72 is of a non-contact type and acquires the user's electroencephalogram, so as to determine whether the user is awake or asleep, or is in which sleep stage. The muscle tone monitoring sensor 73 is of a non-contact type and acquires the user's muscle tone level at his/her neck and upper and lower limbs, for determination of in which sleep stage the user is. The snore monitoring sensors 74 make records about the user's snore sound and rhythm, as a material for determination of in which sleep stage the user is in and the user's sleep apnoea frequency.

A body temperature sensor 75, a pulse sensor 76, breath sensor 77, a blood pressure sensor 78, an oxygen saturation sensor 79, an electrocardiogram sensor 710, and a limb motion sensor 720 at the user's finger backs collect the user's physiological data such as the user's body temperature, pulse, breath, blood pressure, oxygen saturation, electrocardiogram, and limb motion. The data are sent to the central data processing module 3 in a real time manner. The breath sensor 77 uses infrared to detect heave of the user's chest and abdomen when the user inhales and exhales. The detected data are then processed using a particular algorithm to measure the user's breath frequency and breath depth.

The sleep-caring robot turns the finger back to the user's exposed neck, face and hands for measurement.

Figure 6:
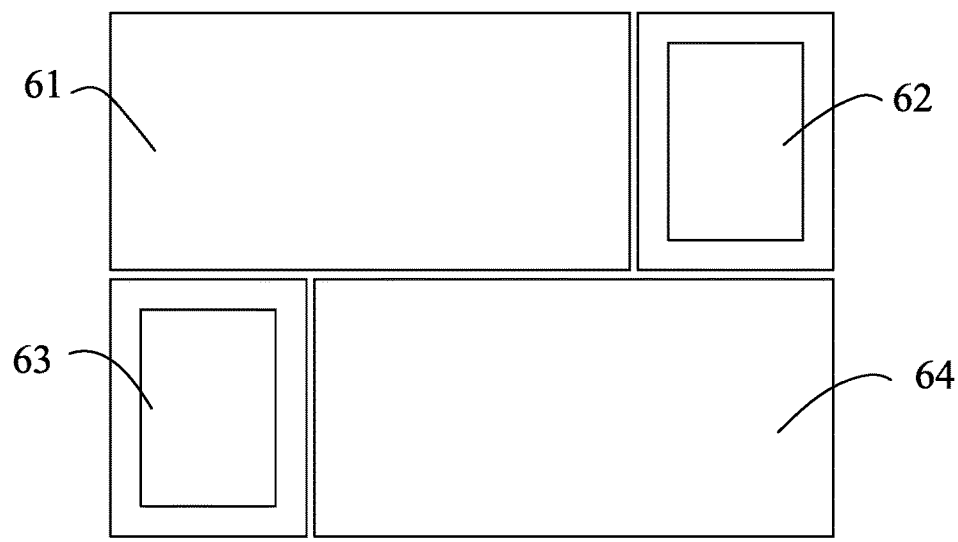
FIG. 6 is a schematic drawing of a smart storage compartment of the sleep-caring robot according to the present invention.

Referring to FIG. 6, the smart storage compartment 6 is divided into an upper-left partition 61, an upper-right partition 62, a lower-left partition 63, and a lower-right partition 64.

The upper-left partition 61 is used to store non-private articles, such as sanitary napkins and paper diapers. The upper-left partition 61 has its side walls and top equipped with sensors, which collect information about articles put in or taken out. The information is then transmitted to the central data processing module 3. The central data processing module 3 acquires data about the types and quantities of articles stored in the upper-left partition 61, and displays the data as a structured data chart in the touch screen inside the transparent partition door in a real time manner.

The lower-right partition 64 is used to store private articles, such as medicine and skincare products, and has a door equipped with a smart lock. The side walls and the top of the lower-right partition 64 are equipped with sensors, which collect information about articles put in or taken out data. The information is then transmitted to the central data processing module 3. The central data processing module 3 acquires data about the types and quantities of articles stored in the lower-right partition 64, and displays the data as a structured data chart in the touch screen inside the opaque partition door in a real time manner.

The lower-left partition 63 is configured as a temperature-controllable chill box, for storing cold drinks. The upper-right partition 62 is configured as a temperature-controllable thermotank, for storing bottled water, drinks, and milk. This partition has sensors installed therein for collecting temperature, pressure, and graphic data. The information is then transmitted to the central data processing module 3. The central data processing module 3 acquires data about the types, quantities and weight of article stored in the upper-right partition 62 and data about the internal temperature of the upper-right partition 62, and displays the data in the touch screen outside the partition door in a real time manner.

The touch screen further has a replenishment button. Pushing the replenishment button leads to commencement of an on-line shopping process.

The touch screen further has a voice button. Pushing the voice button causes the structured data chart information to be broadcasted through the smart speaker 15.

Figure 7:
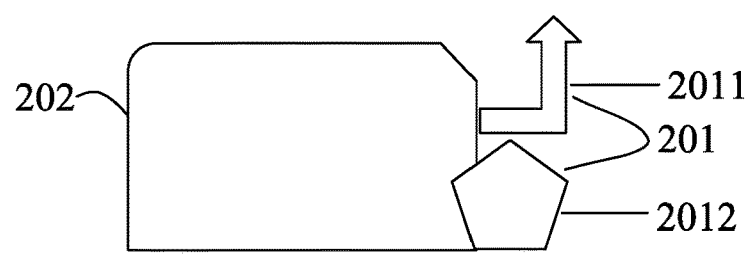
FIG. 7 is a schematic drawing of a power supply of the sleep-caring robot according to the present invention.

Referring to FIG. 7, the power supply 20 includes a charging device 201 and a power-storing device 202. The charging device 201 includes a first device 2011 matching a wired charging pile and a second device 2012 matching a wireless charging zone. When the power-storing device 202 of the sleep-caring robot has its power level lower than a predetermined power threshold, the power supply 20 can automatically go to the wired charging pile or the wireless charging zone to get charged, and returns to a designated standby area when it is fully charged.

The smart appliances connected through the wireless network include a smart air conditioner, a smart air cleaner, a smart toilet, a smart water heater, a smart TV, a smart refrigerator, a smart washing machine, and a smart mosquito killer. Through the appliance control module 14 and the wireless communication module 17, the smart appliances receive and respond to instructions from the central data processing module 3. The smart furniture connected through the wireless network includes a smart closet, a smart bed, a smart mattress, a smart pillow, a smart curtain, a smart door and a smart window. Their smart sensing devices, through the wireless communication module 17, receive and respond to instructions form the central data processing module 3. The user can name, add or delete smart furniture in the central touch screen display 4 or the mobile smart control terminal 10.

The security monitoring devices connected through the wireless network include infrared detectors, smoke detectors, gas detectors, and cameras. They collect data through the wireless communication module 17 and send the data to the central data processing module 3, which shows the data as structured data charts in a real time manner through the central touch screen display 4 and the mobile smart control terminal 10.

The smart wearable devices include a smart wristband, a smart watch, a smart ankle bracelet, a smart earring, a smart eyeshade, a smart earplug, smart glasses, smart pajamas, a smart hat, smart socks, and a smart patch, for monitoring data through the wireless communication module 17 and sending the data to the central data processing module 3. The user may name, add or delete smart wearable devices in the central touch screen display 4 or the mobile smart control terminal 10.

The user may be a young child, a bedridden patient, or a healthy adult.

Figure 8:
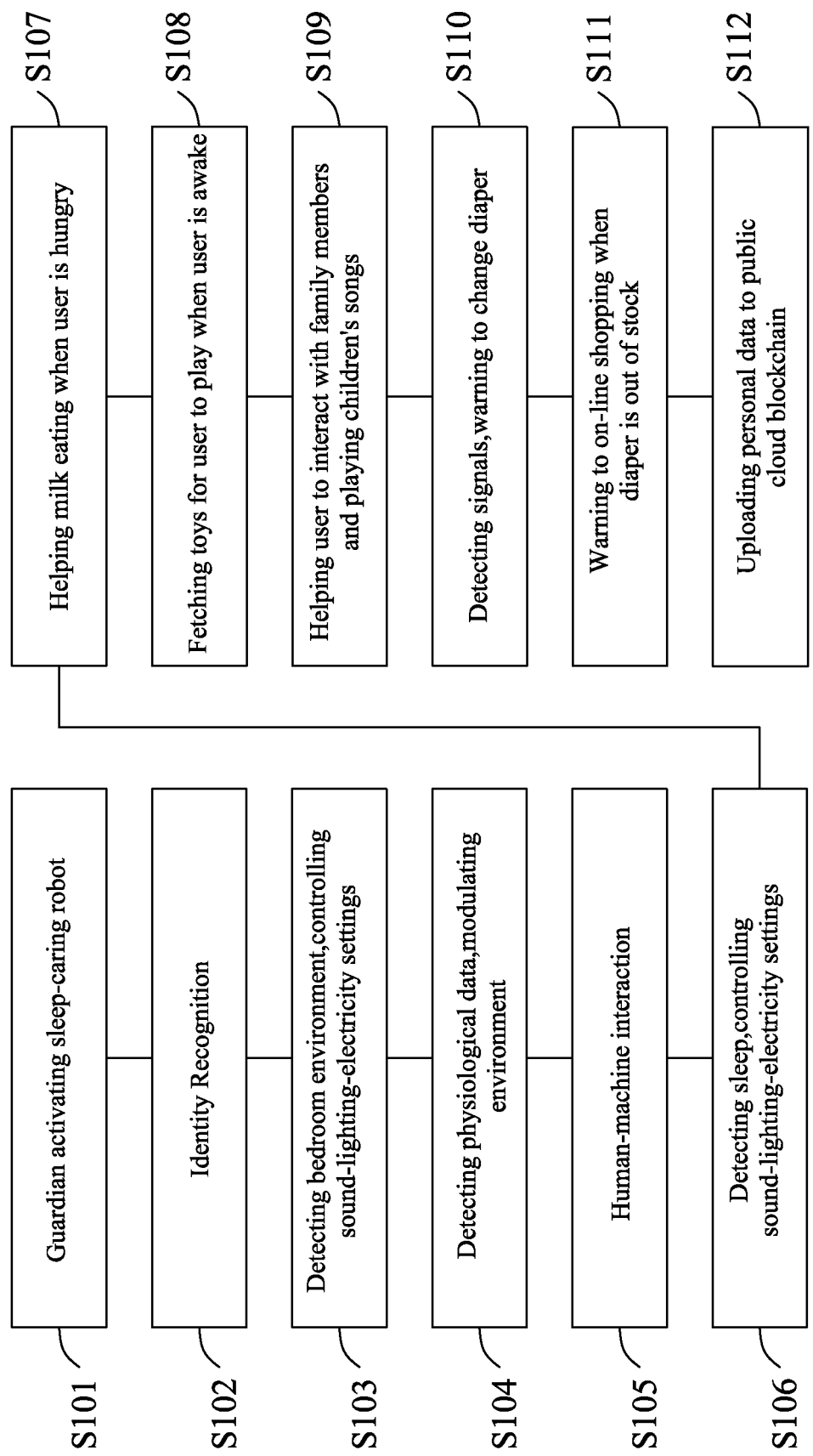
FIG. 8 shows a young child-specific flow of the present invention.

Referring to FIG. 8, a young child-specific sleep-caring service process includes:

S101: a guardian entering a smart contract and getting authorized, near-field or through contracted mobile smart terminal, activating the sleep-caring robot;

S102: the user receiving identity recognition, wherein the user may include a plurality of young children, for which user IDs are created, respectively, for hospital nurseries, kindergarten nurseries, or families with multiple young children;

S103: the sleep-caring robot monitoring bedroom environment, controlling the smart appliances and smart furniture, and adapting bedroom sound, light, temperature, humidity, air environment, and smell to the user's habits or to the mode set by the guardian;

S104: the machine hand 7 adjusting distance to the user and orientation, monitoring the user's physiological data, and determining the user's state according to monitoring data, so as to modulate the bedroom environment in a real time manner;

S105: the guardian using the contracted mobile smart terminal to monitor the user's state in a real time manner, and performing human-machine interaction with the sleep-caring robot;

S106: when the sleep monitoring module detects that the user is about to sleep, the smart speaker 15 playing sleep-facilitating music until the user falls asleep, and then the bedroom being silent with the light dimmed down and the curtain expanded;

S107: when the physiology monitoring module detects that the user is crying for hunger or sending signals alike, the machine hand taking out the feeding bottle that has been stored in the upper-right partition 62 of the smart storage compartment 6 by the guardian, instructing the smart mattress to adjust the user to a half-sitting position, the machine hand delivering the feeding bottle to the user's mouth and helping the user to have milk, after the user finishes his/her milk, the machine hand placing the feeding bottle back to the upper-right partition 62, and having the user adjusted to a sitting position, and after the user burps, instructing the smart mattress to adjust the user to a lying position;

S108: when the sleep monitoring module detects that the user is awake, the machine hand taking out a toy from the smart storage compartment 6 for the user to play, and the guardian playing a video through the central touch screen display 4 for the user to watch;

S109: the user interacting with his/her family members through the smart speaker 15, or listening to children's songs to receive language training;

S110: when the smart patch on the paper diaper detects a signal for diaper change, an alarm being given out to call the guardian to come to the bedroom and take out a spare paper diaper from the smart storage compartment 6 for diaper change;

S111: when the stock of paper diapers in the smart storage compartment 6 is short, a warning being displayed in the display on the partition door of the smart storage compartment 6 to prompt the guardian to activate an on-line shopping process for buying paper diapers by pushing the replenishment button, or the guardian setting a threshold for the minimum quantity of paper diapers in the smart storage compartment 6 so that when the stock is equal to or lower than the threshold, the on-line shopping process for buying paper diapers is activated automatically; and S112: the user's personal data being uploaded to and stored in the blockchain in the public cloud for a third party who is contracted and authorized or the guardian to access.

Figure 9:
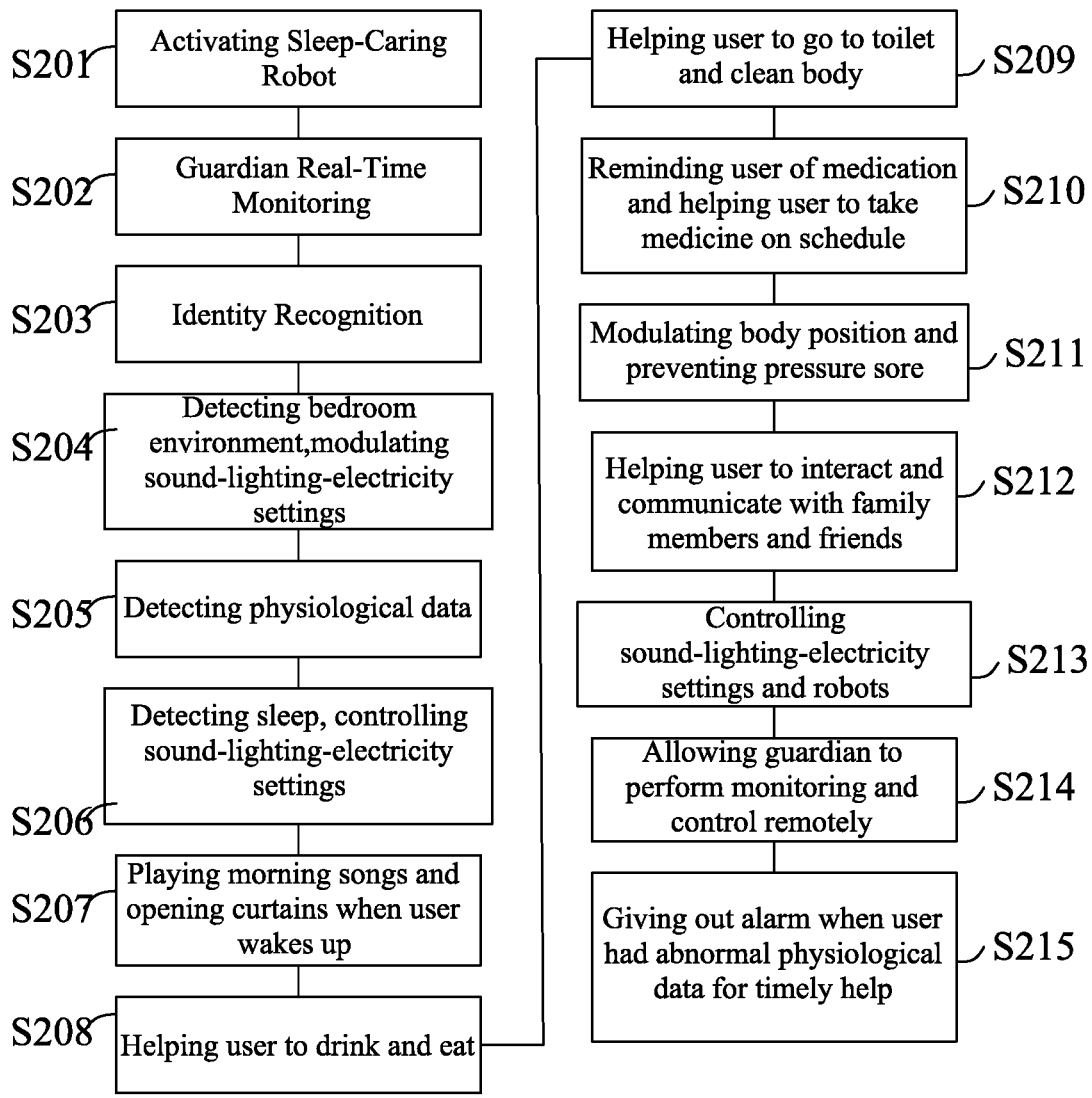
FIG. 9 shows a bedridden patient-specific flow of the present invention.

Referring to FIG. 9, a bedridden patient-specific sleep-caring service process includes:

S201: a guardian entering a smart contract, and the guardian or a user activating the sleep-caring robot;

S202: the guardian using the contracted mobile smart terminal to monitor the user's state in a real time manner, and performing human-machine interaction with the sleep-caring robot;

S203: the user receiving identity recognition, wherein the user may include a plurality of bedridden patients, for which user IDs are created, respectively, for hospital wards, nursing homes, or families with multiple bedridden patients;

S204: the sleep-caring robot monitoring bedroom environment, controlling the smart appliances and smart furniture, adapting sound, lighting, electricity, and air environment to the user's habits or a mode set by the guardian;

S205: the sleep-caring robot monitoring user's physiological data, determining the user's state, according to monitoring data, real time modulating bedroom environment;

S206: when the sleep monitoring module detects that the user is about to sleep, the smart speaker 15 playing sleep-facilitating music until the user falls asleep, and then the bedroom being silent with the light dimmed down and the curtain expanded;

S207: when the sleep monitoring module detects that the user is waking up in the morning, the smart speaker 15 playing morning songs, the light being dimmed up, or the smart curtain being gradually retracted;

S208: when the user asks for drinks and food thorough human-machine interaction, the machine hand taking out food from the thermotank located in the lower-left partition 63 or the upper-right partition 62 of the smart storage compartment 6, instructing the smart mattress to adjust the user to a sitting position, delivering food to the user's mouth, and helping the user to eat;

S209: when the user express his/her intention to urinate and defecate thorough human-machine interaction, the machine hand taking out a pedestal pan from the upper-left partition 61 of the smart storage compartment 6, instructing and working with the family healthcare robot and the smart furniture to help the user to urinate and defecate and to clean the user's perineum;

S210: the machine hand 7 taking out medicine from the lower-right partition 64 of the smart storage compartment 6 and taking out drinking water from the upper-right partition 62 at a predetermined time point as scheduled in a present program, and prompting and helping the user to take medicine in schedule;

S211: the user's smart pajamas monitoring the user's body position to timely modulate the smart mattress in terms of softness and shape, so as to prevent pressure sore caused by prolonged local compression;

S212: the user interacting and communicating with family members and friends through the smart speaker 15 in a real time communication manner;

S213: the user using the human-machine interaction or the mobile smart control terminal to play music through the smart speaker 15 or to play videos or TV programs through the central touch screen display 4, to control the smart appliances, smart furniture, smart security, smart robots connected through the wireless network;

S214: the guardian using a mobile smart terminal for which it enters a contract to communicate with the user in a real time manner for remote monitoring and control the sleep-caring robot; and S215: monitoring the physiological data and when the data go beyond a preset threshold, automatically giving out alarm and notifying the guardian and the relevant contracted third party, so as to aid the user timely.

Referring to FIG. 10, the healthy adult sleep-caring service process includes:

S301: user near-field or contracted mobile smart terminal remote activating the sleep-caring robot;

S302: user identity recognition; when there are a number of users, creating user IDs, respectively;

S303: the sleep-caring robot monitoring bedroom environment, according to user bedroom living habits data or human-machine interaction instructions, and controlling the smart appliances and smart furniture connected through the wireless network, and smart robots to modulate sound, lighting, electricity and air environment;

S304: the sleep-caring robot monitoring user physiological data, determining the user's state, and modulating bedroom environment according to monitoring data in a real time manner;

S305: when the user is awake, he/she being able to use human-machine interaction to control the smart speaker 15 to play music, control the central touch screen display 4 to play videos or TV programs, check security monitoring signals and communicate with his/her partners or the emotional accompanying robot;

S306: when the user is about to sleep, the smart speaker 15 playing sleep-facilitating music until the user falls asleep, and then the bedroom being silent with the light dimmed down and the curtain expanded;

S307: when the user gets up at night and the limb motion sensor 720 detects that the user's body turning to the sitting position from the lying position, the smart sensing night light being dimmed up, and when the user returns to bed to sleep, the smart sensing night light being dimmed down gradually;

S308: when the user feels thirsty, he/she choosing to consume cold drinks in the lower-left partition 63 in the smart storage compartment 6, or warm drinks in the upper-right partition 62;

S309: when the user is waking up, the smart speaker 15 playing morning songs, the light being dimmed up, or the smart curtain being gradually retracted;

S310: the user's smart pajamas monitoring the user's body position to timely modulate the smart mattress in terms of softness and shape, so as to protect the user's body from prolonged local compression;

S311: the user interacting and communicating with his/her family members and friends through the smart speaker 15 in a real time manner;

S312: when the user gets up, providing whether information and working with the smart closet to provide dressing and make-up recommendations;

S313: when the stocks in the partitions of the smart storage compartment 6 are short, the displays on the partition doors of the smart storage compartment 6 showing messages to prompt the user to activate an on-line shopping process by pushing the replenishment button; or the guardian setting a threshold for the minimum quantity of articles stored in the smart storage compartment 6 so that when the stock is equal to or lower than the threshold, the on-line shopping process for buying articles is activated automatically.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A robot-connected IoT-based sleep-caring system, comprising a sleep-caring robot and an IoT (Internet of Things) system;

the sleep-caring robot including a power supply driving module, an obstacle avoiding module, an identity recognition module, a personal data encryption module, built-in sensors, machine arms, an environment monitoring module, a physiology monitoring module, a sleep monitoring module, a voice control module, a light control module, an appliance control module, a central touch screen display, a mobile smart control terminal, a smart storage compartment, a wireless communication module, a central data processing module, a human-machine interface module, and a remote monitoring/interacting module, wherein the environment monitoring module is configured for monitoring bedroom environment of a user, the physiology monitoring module is configured for monitoring physiological data of the user, the central data processing module is configured for learning bedroom living habits of the user, the voice control module and the light control module are configured for adjusting bedroom sound, lighting, electricity to desirable working conditions, and the smart storage compartment is configured for providing bedroom supplies, thereby catering to bedroom activities of the user; and the IoT system including smart appliances, smart furniture, smart wearable devices, a mobile smart terminal, a smart security system, a housekeeping robot, and an emotional accompanying robot that are all interconnected through a wireless network, having its working condition data sent to the central data processing module of the sleep-caring robot through the wireless communication module, and receiving and responding to instructions from the sleep-caring robot.

2. The robot-connected IoT-based sleep-caring system of claim 1, wherein the power supply driving module includes a power supply and a servomotor driving system, the power supply serving to supply electricity, the servomotor driving system serving to drive the sleep-caring robot to perform various acts; the power supply including a charging device and a power-storing device, both located in a lower part of the sleep-caring robot; the charging device matching a wired charging pile and a wireless charging zone, wherein the wired charging pile and the wireless charging zone are for the sleep-caring robot to go to and get charged automatically when the power-storing device has a power level lower than a predetermined power threshold.

3. The robot-connected IoT-based sleep-caring system of claim 1, wherein the obstacle avoiding module includes a positioning unit, an electronic fence, and ultrasonic radars, the positioning unit being based on GPS (Global Positioning System) and Beidou Navigation, the electronic fence defining an area for the sleep-caring robot to work, and providing information of static obstacles in the area defined by the electronic fence, the ultrasonic radars being installed peripherally on the sleep-caring robot, for detecting distances to surrounding obstacle, so that the obstacle avoiding module according to data from the positioning unit and the ultrasonic radar guides the sleep-caring robot away from surrounding dynamic and static obstacles, thereby the positioning unit, the electronic fence and the ultrasonic radars helping the sleep-caring robot to arrive at a predetermined location.

4. The robot-connected IoT-based sleep-caring system of claim 1, wherein the identity recognition module performs real-name authentication using blockchain technology, the user entering a smart contract, creating a personal private key and a personal public key, sending the personal public key, biometric information, and ID (Identity) card information to a blockchain network, so as to generate blocks and acquire a link to the public key certificate, the user inputting the biometric information, and the blockchain network identifying the user by verifying the link to the public key certificate.

5. The robot-connected IoT-based sleep-caring system of claim 1, wherein the personal data encryption module creates a user personal data center using blockchain technology, the user personal data center storing and running personal and family data of the user in a distributed manner; the personal data center, the sleep-caring robot, the Internet, the IoT system, and a public cloud being all connected based on the smart contract for the blockchain authorized by the user, the personal and family data being written into the blocks in a real time manner, and being published to the blockchain in the public cloud with authorization from the user, so as to achieve security isolation of the personal and family data; and a third party having authorization being allowed to access the data.

6. The robot-connected IoT-based sleep-caring system of claim 1, wherein the machine arms are each structurally similar to a human upper limb, and are attached to an upper end of the sleep-caring robot, one at each side, each said machine arm having one end connected to the sleep-caring robot, and an opposite end formed as a machine hand, the machine hand including five fingers, the machine arms receiving instructions from the central data processing module, and being driven by the servomotor to perform acts.

7. The robot-connected IoT-based sleep-caring system of claim 1, wherein the environment monitoring module includes environment monitoring sensors, and an A/D (Analog-to-Digital) conversion circuit, and is installed in a head of the sleep-caring robot, environment data detected by the environment monitoring sensors being sent to the central data processing module; the environment monitoring sensors including but not limited to a temperature sensor, a humidity sensor, a noise sensor, a smoke sensor, a PM (Particulate Matter) 10 sensor, a PM2.5 sensor, a carbon dioxide sensor, a carbon monoxide sensor, and a smell sensor.

8. The robot-connected IoT-based sleep-caring system of claim 1, wherein the physiology monitoring module integrates a plurality of monitoring sensors for collecting physiological data of the user in a non-contact manner, the monitoring sensors including but not limited to a body temperature sensor, a pulse sensor, a breath sensor, a blood pressure sensor, an oxygen saturation sensor, an electrocardiogram sensor, and a limb motion sensor, the physiological data of the user detected by the monitoring sensors being sent to the central data processing module; the monitoring sensors being installed on finger backs of a machine hand, and facing the user's neck and hands when conducting detection; the breath sensor collecting infrared data about heave of the user's chest and abdomen during inhalation and exhalation, so that breath frequency and breath depth of the user are able to be calculated.

9. The robot-connected IoT-based sleep-caring system of claim 1, wherein the sleep monitoring module includes an image sensor installed in a head of the sleep-caring robot, and a brainwave monitoring sensor, a muscle tone monitoring sensor, and a snore monitoring sensor installed on finger backs of a machine hand, all of a non-contact type;
the image sensor having a visible-light image capturing mode and an infrared image capturing mode sending image data of the user to the central data processing module, for real-time recognition and determination of body location information of the user;
the brainwave monitoring sensor acquiring electroencephalogram of the user, and sending data to the central data processing module, for determination of whether the user is awake or asleep, and is in which sleep stage;
the muscle tone monitoring sensor acquiring a muscle tone level at the user's neck, and upper and tower limbs, and sending data to the central data processing module, for determination of in which sleep stage the user is; and
the snore monitoring sensor acquiring data about the user's snore sound and rhythm, and sending the data to the central data processing module, for determination of in which sleep stage the user is and times of the user's sleep apnoea.

10. The robot-connected IoT-based sleep-caring system of claim 1, wherein the voice control module includes a voice hearing unit and a smart speaker, and is installed in a head of the sleep-caring robot, the voice hearing unit collecting voice signals from the user so as to obtain voice data, and sending the data to the central data processing module through the wireless communication module, recognizing speaking voice, understanding language, and giving out instructions, the smart speaker receiving the instructions through the wireless communication module, and executing options of content to be played and playing methods; the smart speaker being further connected to the sleep monitoring module through the wireless communication module, so as to adjust the content to be played and volume according to the sleep stage and following a predetermined program; and the predetermined program being set by the user or a guardian.

11. The robot-connected IoT-based sleep-caring system of claim 1, wherein the light control module is installed in a head of the sleep-caring robot, and includes a smart sensing unit, a control unit and smart lamps; the smart sensing unit including a luminous intensity sensor, a color sensor, and a color temperature sensor, and transmitting data collected to the central data processing module, so as to control the smart lamps through the control unit according to triggering conditions of scene modes; the control unit allowing the user to name, add or delete each said smart lamp at the central touch screen display; and the control allowing each said lamp to be turned on, turned off, dimmed and changed in color; and the scene modes including human-machine interaction, clock setting, sleep stage, and control of a third party mobile smart terminal, wherein human-machine interaction is set as the first priority, and clock setting is set as the second priority, while an authorized third party making control through the mobile smart terminal with a contract is set as the third priority.

12. The robot-connected IoT-based sleep-caring system of claim 1, wherein the appliance control module is installed in a head of the sleep-caring robot, and is rotatable up to 180 degree in both directions, in which the appliance control module performs near-field control using Bluetooth and infrared, and performs far-field control using Wi-Fi.

13. The robot-connected IoT-based sleep-caring system of claim 1, wherein the central touch screen display is installed in an upper front part of a trunk of the sleep-caring robot, for displaying information of aggregate data, security monitoring signals, TV (Television) signals, video playing, and touch operation.

14. The robot-connected IoT-based sleep-caring system of claim 1, wherein the smart storage compartment is located in a lower-middle part of a trunk of the sleep-caring robot, and is divided into an upper-left partition, an upper-right partition, a lower-left partition, and a lower-right partition; the upper-left partition storing non-private articles, with its side walls and top equipped with sensors, which collect information about articles put in or taken out, the information then being transmitted to the central data processing module, for the central data processing module to retrieve information about types and quantities of the articles stored, and to show the information as a structured data chart displayed in a touch screen located outside a transparent door of the partition;

the lower-right partition for storing private articles, with its door equipped with a smart lock, and with its side walls and top equipped with sensors, which collect information about articles put in or taken out, the information then being transmitted to the central data processing module, for the central data processing module to retrieve information about types and quantities of the articles stored, and to show the information as a structured data chart displayed in a touch screen located inside an opaque door of the partition in a real time manner;

the lower-left partition being configured as a temperature-controllable chill box, the upper-right partition being configured as a temperature-controllable thermotank, the partition containing therein a temperature sensor, a pressure sensor, and an image recognition sensor, and transmitting data collected to the central data processing module, for the central data processing module to retrieve information about types and quantities and weight of the articles stored, and internal temperature data, and to show the information in a touch screen outside a door of the partition; and the touch screen further having a replenishment button, and pushing the replenishment button leading to commencement of an on-line shopping process; and the touch screen further having a voice button, and pushing the voice button making the smart speaker broadcast information of the structured data chart.

15. The robot-connected IoT-based sleep-caring system of claim 1, wherein the central data processing module is located in an upper part of a trunk of the sleep-caring robot, for receiving data detected by the built-in sensors of the sleep-caring robot and external sensors, merging information from multiple sensors, perceiving states of the sleep-caring robot, bedroom environment, of the user and security, through the human-machine interface module, the central data processing module smartly controlling the sleep-caring robot, the smart appliances connected through the wireless network, the smart furniture, the housekeeping robot, and the emotion robot; and according to the user's instructions to send raw data as collected and processed data to the blockchain in the public cloud.

16. The robot-connected IoT-based sleep-caring system of claim 1, wherein the human-machine interaction interface module includes a human-machine interface device, interaction technology, monitoring technology, remote operation technology, communication technology, completing cognitive learning, automatic organization, fuzzy information processing; and the interaction technology includes recognition of user-initiated requests and recognition of non-user-initiated requests, the user-initiated requests including voice, lip language, gestures, controllers, and remote control; and the non-user-initiated requests including setting specific triggering conditions, and feedback from the user's smart wearable.

17. The robot-connected IoT-based sleep-caring system of claim 1, wherein the human-machine interaction interface further includes a brain-computer interface mode, which collects the user's brain bioelectric activity signals through non-invasive sensors, and transmits data to the central data processing module, for control of the sleep-caring robot.

18. The robot-connected IoT-based sleep-caring system of claim 1, wherein the smart appliances connected through the wireless network include a smart air conditioner, a smart air cleaner, a smart toilet, a smart water heater, a smart TV a smart refrigerator, a smart washing machine, and a smart mosquito killer, and receive and respond to instructions from the central data processing module through the appliance control module.

19. The robot-connected IoT-based sleep-caring system of claim 1, wherein the smart furniture connected through the wireless network includes a smart closet, a smart bed, a smart mattress, a smart pillow, a smart curtain, a smart door and a smart window, its smart sensing device, through the wireless communication module, receiving and responding to instructions from the central data processing module; and the user being allowed to name, add or delete the smart furniture in the central touch screen display.

20. The robot-connected IoT-based sleep-caring system of claim 1, wherein the smart wearable devices include a smart wristband, a smart watch, a smart ankle bracelet, a smart earring, a smart eyeshade, a smart earpiece, smart glasses, smart pajamas, a smart hat, smart socks, and a smart patch, and data they detect are sent to the central data processing module through the wireless communication module; and the user being allowed to name, add or delete the smart wearable devices in the central touch screen display.

21. The robot-connected IoT-based sleep-caring system of claim 1, wherein the mobile smart control terminal is a remote control for the sleep-caring robot, and also works as a smartphone.

22. The robot-connected IoT-based sleep-caring system of claim 1, wherein the remote monitoring/interacting module is installed in a head of the sleep-caring robot, which allows an authorized third party to acquire data of the sleep-caring robot using the mobile smart terminal for which it enters a contract through the wireless communication module in a real time manner, so as to operate and monitor the sleep-caring robot remotely.

23. The robot-connected IoT-based sleep-caring system of claim 1, wherein the learning bedroom living habits of the user is achieved by having the sleep-caring robot recognize and analyze the user's bedroom sound, lighting and electricity environment data, physiology monitoring data, sleep behavior data, human-machine interaction data, supply consumption data, and event-specific triggering data stored in the blockchain in the public cloud, sense the user's bedroom living habits, perform self-learning, perform autonomous decision-making, set resulting decision as benchmarks, collect the user's feedback data about the benchmarks set by the sleep-caring robot based on its autonomous decision-making, identify differences, perform self-learning, perform autonomous decision-making, and repeat, so as to achieve harmony between the user and the sleep-caring robot.

24. The robot-connected IoT-based sleep-caring system of claim 1, wherein the user is a young child, a bedridden patient, or a healthy adult, and includes one or more persons, in which when the user includes plural persons, identity recognition and physiological data monitoring are made thereto respectively.

25. The robot-connected IoT-based sleep-caring system of claim 24, wherein a young child-specific sleep-caring service process includes: a guardian entering a smart contract, activating the sleep-caring robot; performing identity recognition; the sleep-caring robot monitoring bedroom environment, adapting sound, lighting, electricity and air environment to a set mode; the sleep-caring robot monitoring user physiological data, determining the user's state, adjusting sleeping environment in a real time manner, a smart speaker playing music until the user falls asleep, stopping music playing and turning off light; when the user cries for hunger, a machine hand taking out a feeding bottle, helping the user to have milk, taking out a toy for the user to play; the mobile smart terminal of the guardian showing the user's state in a real time manner; and a smart patch monitoring data, giving out alarm, warning the guardian to change the user's diaper.

26. The robot-connected IoT-based sleep-caring system of claim 24, wherein a bedridden patient-specific sleep-caring service process includes: activating the sleep-caring robot; performing identity recognition; the sleep-caring robot monitoring bedroom environment, adapting sound, lighting, electricity environment to the user's habits or a mode set by the user; the sleep-caring robot monitoring the user's physiological data, adjusting bedroom environment in a real time manner; a smart speaker playing music until the user falls asleep, stopping music playing and turning off light; when the user feels hungry, a machine hand taking out food, helping the user to eat and drink; when the user excretes, instructing and helping a family healthcare robot and the smart furniture to clean excrement and clean the user's perineum; according to a set program, taking out medicine and drinking water and prompting and helping the user to take medicine timely; monitoring the user's body position, adjusting rigidity of the smart mattress timely so as to prevent pressure sore caused by prolonged local compression; the user interacting with family members and friends through the smart speaker; a guardian using the mobile smart terminal for which it enters a contract to communicate with the user in a real time manner for remote monitoring and control; and when abnormal physiological data are detected, reporting to a competent third party for timely assistance.

* * * * *